US007384652B2

(12) United States Patent
Boskey et al.

(10) Patent No.: US 7,384,652 B2
(45) Date of Patent: Jun. 10, 2008

(54) COMPLEXED-ACIDIC-PHOSPHOLIPID-COLLAGEN COMPOSITES FOR BONE INDUCTION

(75) Inventors: Adele L. Boskey, North Caldwell, NJ (US); Helen Tudor, New York, NY (US)

(73) Assignee: New York Society for the Ruptured and Crippled Maintaining the Hospital for Special Surgery, New York, NY (US)

(*) Notice: Subject to any disclaimer, the term of this patent is extended or adjusted under 35 U.S.C. 154(b) by 617 days.

(21) Appl. No.: 10/603,478

(22) Filed: Jun. 24, 2003

(65) Prior Publication Data

US 2004/0076663 A1 Apr. 22, 2004

Related U.S. Application Data

(60) Provisional application No. 60/391,257, filed on Jun. 24, 2002.

(51) Int. Cl.
*A61K 31/39* (2006.01)
*A61K 9/127* (2006.01)

(52) U.S. Cl. ................ 424/450; 424/190.1; 424/238.1; 424/2; 514/2

(58) Field of Classification Search ................ 424/450, 424/190.1, 238.1
See application file for complete search history.

(56) References Cited

U.S. PATENT DOCUMENTS 4,294,753 A 10/1981 Urist
4,434,094 A 2/1984 Seyedin et al.
4,440,750 A 4/1984 Glowacki et al.
4,455,256 A 6/1984 Urist
4,578,384 A * 3/1986 Hollinger ....................... 514/8
4,627,982 A 12/1986 Seyedin et al.
4,780,450 A 10/1988 Sauk et al.
5,492,697 A * 2/1996 Boyan et al. ............ 623/16.11
5,904,718 A 5/1999 Jefferies
5,972,385 A 10/1999 Liu et al.
6,197,759 B1 3/2001 Esswein et al.
6,261,586 B1 7/2001 McKay
6,311,690 B1 11/2001 Jefferies
6,344,496 B1 2/2002 Niederauer et al.

FOREIGN PATENT DOCUMENTS

WO WO 94/15653 7/1994

OTHER PUBLICATIONS

"Difference in thermal stability of type-I and type III collagen from rat skin", Danielsen, C., Biochem. J, 1982, 203, 323-326.*
"Collagen degradation in rat skin but not in intestine during rapid growth: Effect on collagen types I and III from skin", Klein et al., Proct. Natl. Aca. Sci. USA, vol. 74, No. 4, pp. 1436-1439, 1977.*
"Hagfish and lancelet fibrillar collagens reveal that ype II collagen-based cartilage evolved in stem vertebrates", Zhang et al., PNAS, 2006, vol. 103, No. 45, pp. 16829-16833.*
U.S. Appl. No. 60/391,257, filed Jun. 24, 2002, Boskey.
Anderson, Clinical Orthopaedics and Related Research, 1995, 314:266-280.
Anghileri, Z. Krebsforsch. 1973, 79:148-156.
Boskey and Posner, Calcif. Tissue Res. 1976, 19:273-283.
Boskey and Posner, Calcif. Tissue Res. 1977, 23:251-258.
Boskey and Posner, Calcified Tissue Int. 1982, 34:S1-S7.
Boskey et al., Calcif Tissue Int. 1996, 58:45-51.
Boskey, The Journal of Physical Chemistry, 1989, 93:1628-1633.
Bostrom et al., J Orthop Res. 1995; 13:357-367.
Boyan et al., Steroids 2001, 66:363-374.
Costa et al., American Journal of Dentistry, 2000;13(2):81-87.
Cotmore et al., Science 1971, 172:1339-3341.
Ennever et al., Cytobios. 1984, 39:151-157.
Goldberg and Boskey, Prog. Histochem. Cytochem. 1996, 31(2):1-187.
Hunter et al., Endod Dent Traumatol. 1998;14:112-118.
Lane et al., Clin. Orthop. 1999, 361:216-227.
Neufeld and Boskey, Bone 1994, 15(4): 425-430.
Raggio et al., J Bone and Min Res. 1986, 1(5): 409-415.
Schmitz et al., Acta Anat (Basel) 1990;138:185-192.
Sloan et al., Arch Oral Biol. 2000; 45:173-177.
Tintut et al., Current Opinion in Lipidology, 2001, 12:555-560.

* cited by examiner

*Primary Examiner*—Brian Kwon
(74) *Attorney, Agent, or Firm*—Darby & Darby

(57) ABSTRACT

The present invention provides a composition for osteoinduction, which comprises a complexed-acidic-phospholipid complex containing calcium, phospholipid, and inorganic phosphate combined with collagen in a composite form. The composition is effective to promote new bone formation upon introduction of the composition into various osseous defects.

24 Claims, 4 Drawing Sheets

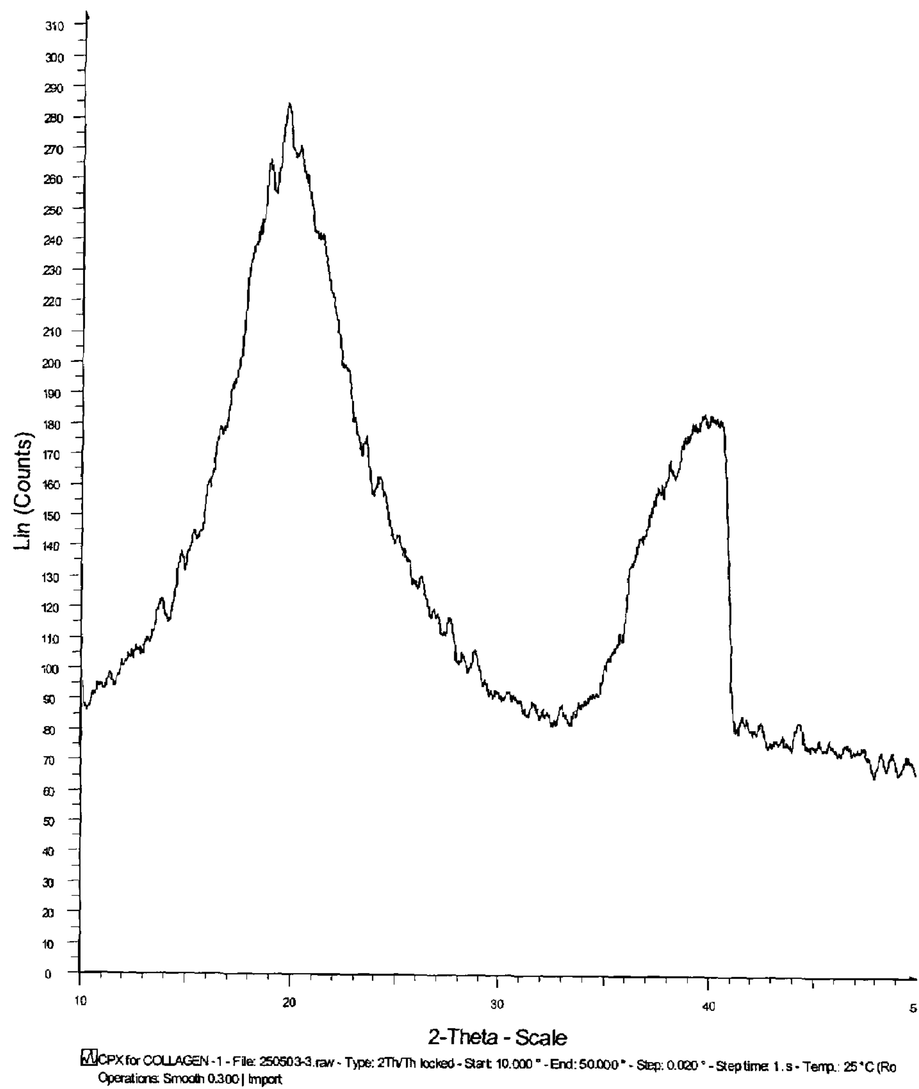
Figure 2. *Diffraction pattern of Acidic Ph spholipid Complex*
(Radiation: CuK$\alpha$; $\lambda$:1.54186)

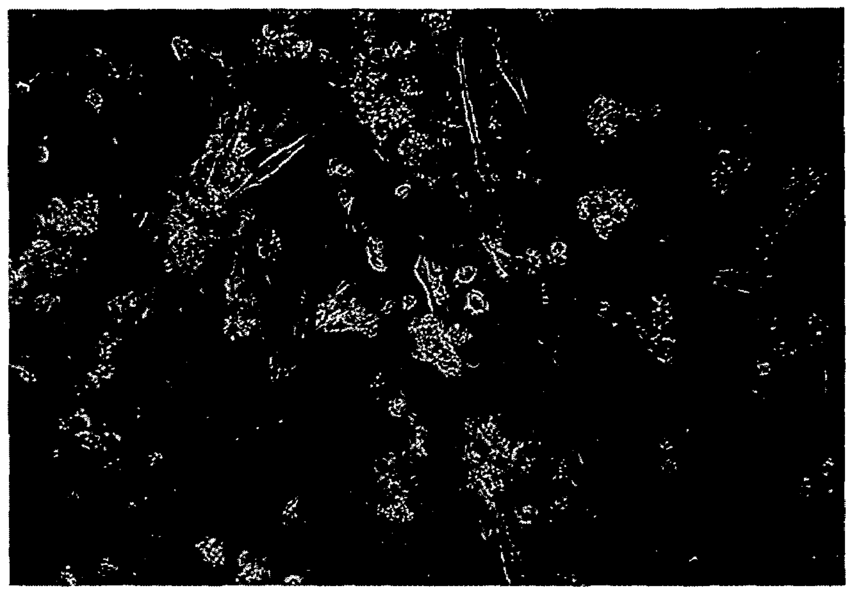
Fig. 3 COLLPLEX I with MG 63 cells. Incubation time: 44 hours
(1500 μg CPLX/ 5 mg collagen prepared in an acidic environment)
300X
Fig. 4 COLLPLEX I I with MG 63 cells. Incubation time: 48 hours
(1500 μg CPLX/ 5 mg collagen prepared in a basic environment)
300X

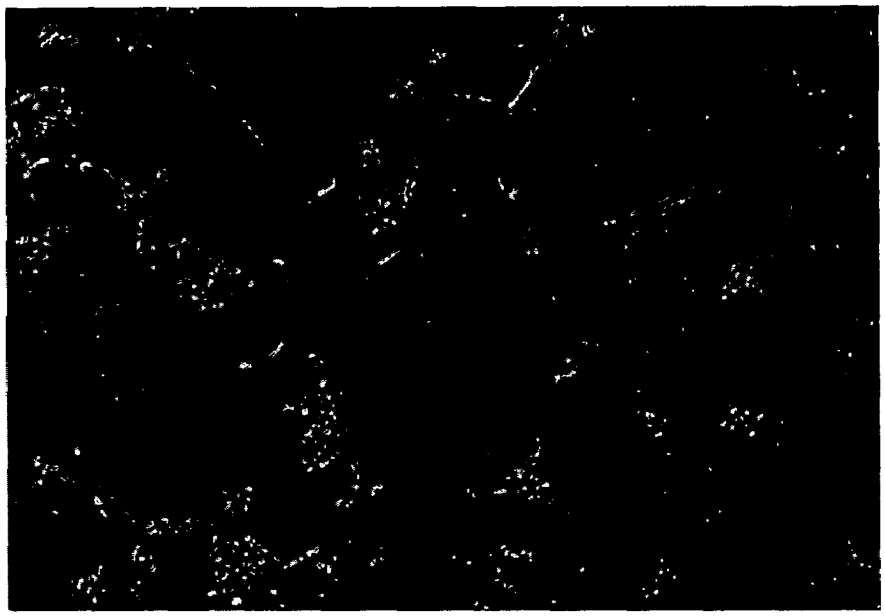
Fig. 5 Fibronectin with MG 63 cells. Incubation time: 44 hours
300X
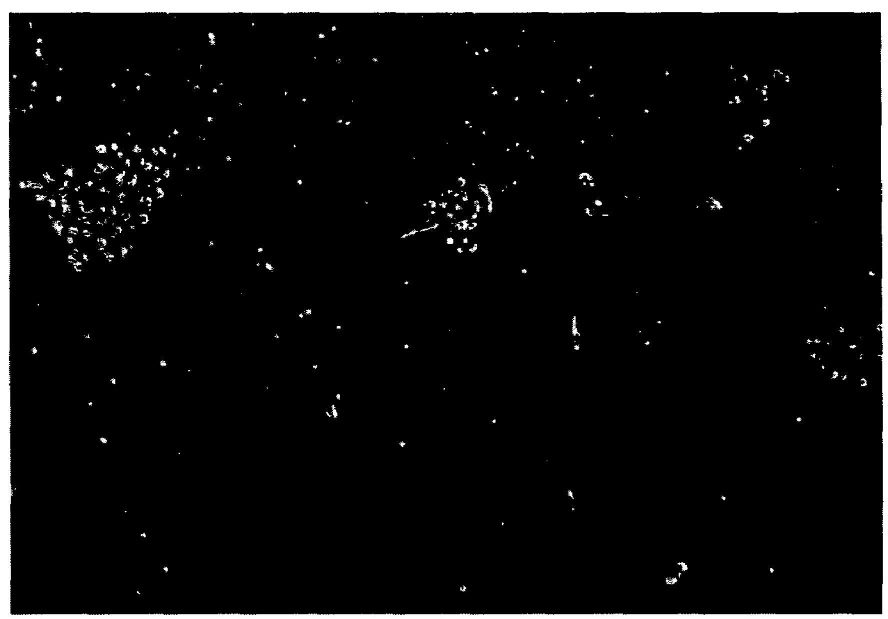
Fig. 6 Negative control (PBS buffer) with MG 63 cells. Incubation time: 44 hours
300X

COMPLEXED-ACIDIC-PHOSPHOLIPID-COLLAGEN COMPOSITES FOR BONE INDUCTION

CROSS-REFERENCE TO RELATED APPLICATIONS

This application claims priority under 35 U.S.C. § 119, based on U.S. Provisional Application Ser. No. 60/391,257, filed Jun. 24, 2002, the entire disclosure of which is hereby incorporated by reference.

FIELD OF THE INVENTION

The present invention is directed to a composite composition, and to a method of using the composition for osteoinduction. Specifically, this invention relates to a complexed-acidic-phospholipid-collagen composite that is used to promote bone growth.

BACKGROUND OF THE INVENTION

There have been a number of materials studied to initiate bone repair and/or to restore or replace missing bone. These studies have been undertaken in an effort to address the problem of stimulating formation of bone at specific sites.

Among the approaches used to address this problem is a conformational method in which an implant material, usually made of metal, ceramic or other inorganic material in a configuration intended to mimic the form of the missing bone, is inserted into the site in which bone replacement is required. With the technique, there is a risk that the host will reject the implant material or that the implant will fail to become integrated with normal skeletal tissue. Some ceramic materials such as ceramic tricalcium phosphate, although acceptably biocompatible with the host and bone, when used as an implant, appear to lack sufficient mechanical properties of bone for general utility. As a result, the bone does not consistently grow into, and become incorporated, within the implant.

Metallic and plastic implants are widely used but are limited in that their mechanical properties do not match that of bone, and the wear debris associated with these implants is known to cause osteolysis. Newer materials (titanates, silicates) can mimic the porosity of bone, and hence allow cellular incorporation, but the implants persist in the body. Calcium phosphate ceramics can also mimic bone porosity, and some of these are resorbable; but their reported success is limited. Calcium phosphate implants which mimic bone have been used in conjunction with proteins and growth factors, but these proteins are degraded more rapidly than the implant, in many cases before cells have penetrated the implant. Collagen implants persist in the tissues, and support the incorporation of cell binding factors; however these factors are rapidly degraded, and may be altered by sterilization.

Another approach, referred to as osteoconduction, involves substituting the missing bone tissue with a matrix which functions as a support into which the new bone growth can occur. The matrix attracts the cells committed to an osteogenic pathway, and the new bone grows in and through the matrix. Allogeneic (non-host) bone grafts are used for this method, however there is a high failure rate. Even when the allogeneic bone grafts are accepted by the host, healing periods for consolidation and capacity for mechanical stress are of comparatively long duration compared to autogeneic (host) bone grafting. The use of allogeneic bone also presents the issue of transmissible viral agents.

A third method for initiating bone repair involves the process known as osteoinduction, which occurs when a material induces the growth of new bone from the host's undifferentiated cells or tissues, usually around a temporary matrix. A number of compounds are disclosed as having such a capacity. See for example, U.S. Pat. No. 4,440,750 to Glowacki, U.S. Pat. Nos. 4,294,753 and 4,455,256 to Urist, and U.S. Pat. Nos. 4,434,094 and 4,627,982 to Seyedin et al. The most effective of these compounds appear to be proteins which stimulate osteogenesis. However, when synthesized from natural sources they are present in extremely low concentrations and require large amounts of starting material to obtain even a minute amount of material for experimentation. The availability of such proteins by recombinant methods may eventually make the use of such proteins per se of more practical value. However, such proteins will still need to be delivered to the desired site in an appropriate matrix.

Acidic phospholipids form unique complexes when incubated in the presence of inorganic phosphate and calcium (Boskey and Posner, Calcif. Tissue Res. 1976, 19:273-283; Boskey and Posner, Calcified Tissues Int. 1982, 34:s1-s7; Cotmore et al., Science 1971, 172:1339-41; Goldberg and Boskey, Prog. Histochem. Cytochem. 1996, 31(2):1-187). These complexes exist in mineralizing tissues as part of the "nucleational core" of extracellular matrix vesicles, the site of initial mineral deposition in cartilage, mantle dentin, and in newly forming bone (Anderson, Clin. Orthop. 1995, 314:266-80). They are also found associated with dystrophic apatite deposition, and their in situ formation is regulated by the same factors that promote bone formation (Tintut et al., Curr. Opin. Lipidol. 2001, 12:555-60; Boyan et al., Steroids 2001, 66:363-74). These complexes induce hydroxyapatite formation in vitro in the absence and presence of cells, and when implanted in vivo. Both the acidic phospholipids themselves (Ennever et al., Cytobios. 1984, 39:151-7) and the acidic phospholipid complexes bind with high affinity to collagen, and when bound are still able to induce mineral deposition (Boskey, J. Phys. Chem. 1989, 93:1628-1633).

Collagens are a class of naturally occurring biomaterials suitable for use in bone regeneration. A major protein constituent of connective tissue, collagen has been widely used in various medical and surgical applications such as for surgical prostheses and graft fabrication. In addition, collagen-based matrices have been used in bone grafting. Type I collagen has good cell adhesive properties, in particular, for bone forming osteoblast cells. Collagen has the capacity to serve both as an active or inert scaffold material for growth. Thus, compositions containing collagen and various forms of calcium phosphate directed to healing and bone growth have been disclosed. For example, U.S. Pat. No. 4,780,450 to Sauk et al. discloses a composition for bone repair comprising particulate polycrystalline calcium phosphate ceramic, a phosphophoryn calcium salt and a type I collagen in a weight ratio of 775-15:3-0.1:1. The ceramic particles are disclosed as being dense hydroxyapatite about 1 to 10 microns in diameter or larger dense hydroxyapatite ceramic particles greater than about 100 microns in diameter.

Similarly, PCT Application WO 94/15653 to Ammann et al. discloses formulations comprising tricalcium phosphate (TCP), TGF-β and collagen. The TCP is disclosed as being a delivery vehicle for the TGF-β such that the TCP is of the particle size greater than 5 microns and preferably greater than about 75 microns. However, the use of solubilized collagen and collagen sheets and blocks for repair of osseous defects in bone and full thickness defects in cartilage have been troubled by the rapid degradation or loss of growth factors and peptides linked to these materials to stimulate osteointegration, and by the loss of these peptides during sterilization. The in vitro nucleation of apatite by the acidic phospholipid complex and collagen composite has been demonstrated in the absence of cells (Boskey, J. Phys. Chem. 1989, 93:1628-1633).

To date, attempts have been made to add bone-inducing substances (i.e., growth factors, peptides) to collagen to promote osteoinduction. However, these attempts have initiated the osteoinduction process with bone (demineralized) rather than collagen. In addition, sterilization techniques may compromise the structural and biochemical properties of the growth factor complexes. Therefore, there exists a need for an osteoinductive material which remains stable after sterilization and advantageously provides reliable bone growth.

SUMMARY OF THE INVENTION

The present invention provides a stable and reliable composite composition made of an acidic phospholipid complex and collagen, wherein the complex comprises calcium, phospholipid, and inorganic phosphate.

In a further aspect of the invention, a method is provided to prepare an acidic phospholipid complex, wherein the method includes:

a) adding two aqueous buffers to phosphatidylserine to form an aqueous solution;
b) vortexing the solution under vacuum in excess of 635 mm Hg;
c) freezing the solution rapidly under vacuum;
d) thawing the solution;
e) extracting the formed complex from the solution in chloroform:methanol; and
f) drying the complex under nitrogen and then storing under vacuum.

In a further embodiment, the invention provides a method of preparing a composition for osteoinduction which steps include:

a) dissolving collagen in acetic acid to form a solution;
b) adding the solution to complexed acidic phospholipid dried under nitrogen to form a mixture;
c) vortexing the mixture under vacuum;
d) freezing the mixture under vacuum to form a solid;
e) thawing the solid; and
f) increasing pH to 7.4 with an appropriate buffer.

In another embodiment, the invention provides a method of preparing a composition for osteoinduction which steps include:

a) suspending dried complexed acidic phospholipid in PBS buffer to form a solution;
b) introducing collagen into the solution;
c) freezing the solution under vacuum;
d) thawing the solid; and
e) increasing pH to 7.4 with an appropriate buffer, resulting in a gel formed composite.

In further aspects of the invention, a method is provided for inducing the growth of bone which includes applying an effective growth stimulating amount of a complexed acidic phospholipid collagen composite at a site in need of desired mineralized tissue growth.

These and other aspects of the invention are discussed more in the detailed description, examples, and drawings.

BRIEF DESCRIPTION OF DRAWING

FIG. 2 presents an x-ray diffraction pattern of the acidic phospholipid complex. The x-axis represents a 2-theta-scale; the y-axis represents the number of counts.

FIG. 3 is an optical micrograph, at a magnification of 300×, which shows the effect of the composite prepared in an acidic environment on MG63 cells after incubation for a 44 hour period. The micrograph shows that cells are adhering and are proliferating.

FIG. 4 is an optical micrograph, at a magnification of 300×, which shows the effect of the composite prepared in a basic environment on MG63 cells after incubation for 48 hours. The micrograph shows that cells are adhering and are proliferating.

FIG. 5 is an optical micrograph, at a magnification of 300×, which shows the effect of Fibronectin on MG63 cells after incubation for 44 hours.

FIG. 6 is an optical micrograph, at a magnification of 300×, which shows that with a negative control, after 44 hours incubation, the MG63 cells remain only in clumps and there appears to be virtually no adherence or proliferation of the cells.

DETAILED DESCRIPTION

Figure 1:
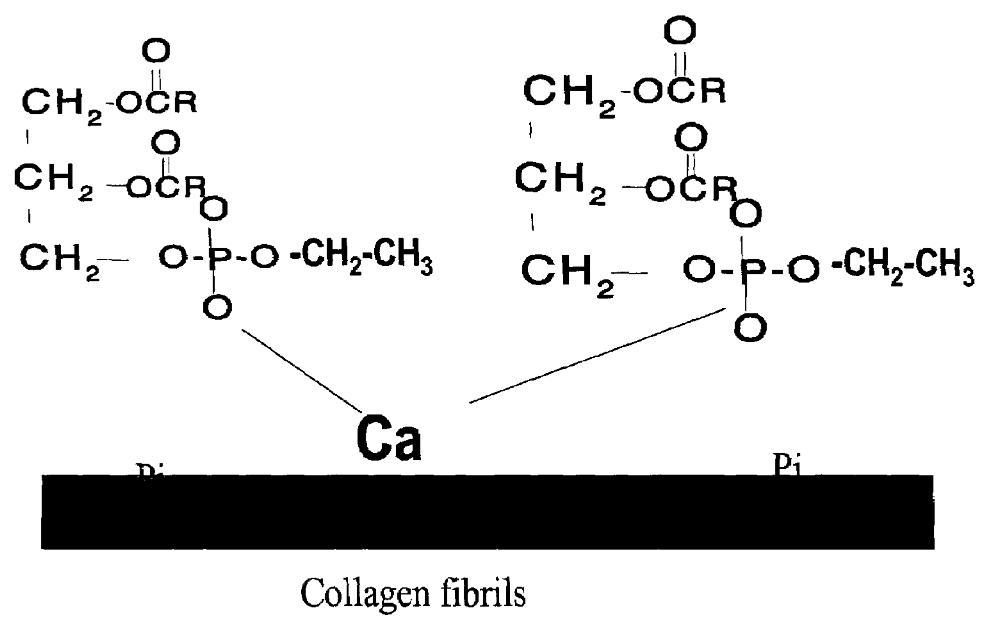
FIG. 1 presents a schematic drawing of the structure of complexed acidic phospholipid on a collagen backbone. The "R"s indicate fatty acids of chain length greater than 12. The "Pi" represents the inorganic phosphate in the complex, as distinct from the organic phosphate that is part of the phospholipids. This drawing is not made to scale as the complexed acidic phospholipid is much smaller than the collagen fibril dimension and the precise mechanism of interaction between the complexed acidic phospholipid and the collagen is not known.

The present invention provides a complexed-acidic-phospholipid-collagen composite that is useful for osteoinduction. According to the invention, the acidic phospholipid complex is bound to a collagen to form a composite, which promotes the desired bone growth without the disadvantages of the prior art. The composite material of the present invention avoids any rejection of implant material and permits consistent bone growth across the region in need of the growth without the disadvantages of rapid degradation of the composite material or unstable support of bone growth due to degrading materials. Furthermore, the composition of the invention is cost-effective relative to other bone induction compositions.

The terms used in this specification generally have their ordinary meanings in the art, within the context of this invention and in the specific context where each term is used. Certain terms are defined below to provide additional guidance in describing the compositions and methods of the invention and how to make and use them.

As used herein, the term "complex" refers to one component of the composite used for bone induction. The complex itself contains three ingredients, namely calcium, phospholipid, and phosphate.

As used herein, the term "collagen" refers to one of the components of the composite of the invention. The collagen can be one of type I, type II and type IX collagens, or combinations thereof, depending on the application of the composite.

As used herein, the term "composite" refers to the material of the acidic phospholipid complex, as defined above, bound to collagen. The composite is used as the structure which is implanted into the area of needed bone growth to initiate the osteoinduction.

As used herein, the term "osteoinduction" refers to bone induction or to the initiation of bone growth that occurs when a material induces undifferentiated cells to initiate bone growth, frequently around a temporary or permanent matrix.

As used herein, the term "regeneration" refers to reconstitution or reproduction of a lost or injured body part. In the present invention, the regeneration refers to the growth of lost bone or mineralized tissue type.

As used herein, the term "site of desired growth" refers to the various mineralized tissue types with which the present invention can be employed. These include but are not limited to long, flat, and endochondral bones, calcifying cartilage, dentin, and cementum. The site of desired growth includes a site within any mammal. In a preferred embodiment, the site of desired growth refers to a site in a human.

As used herein, the term "matrix" generally refers to a structure providing support for osteoinduction by attracting osteoblast cells for proliferation of bone consisting of the collagen combined with the acidic phospholipid complex.

As used herein, the term "mineralization" refers to the deposition of a physiological calcium phosphate (apatite) material in association with a matrix.

As used herein, the term "implant" refers to any soft tissue or bone implant in the body of a mammal. These include, but are not limited to dental implants, osteochodral autografts, tissue scaffolds, and bone regeneration fillers.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The acidic-phospholipid complex of the present invention is a calcium-phospholipid-phosphate complex. In one embodiment, the complex comprises calcium chloride, phosphatidylserine, and ammonium acid phosphate. The components of the complex may be present in the molar ratio of 45-55 parts calcium:35-45 parts phospholipid:5-15 parts inorganic phosphate, respectively. In a preferred embodiment, these components are present in a molar ratio of about 47-53 parts calcium:38-42 parts phospholipid:8-12 parts inorganic phosphate, respectively. In a more preferred embodiment, the molar ratio of calcium, phospholipid, and inorganic phosphate is 50:40:10, respectively (See FIG. 1). In other embodiments, the calcium may be a soluble calcium salt of any weak or strong acid. Examples of the calcium components of the present invention includes, but is not limited to, calcium chloride, calcium nitrate or calcium acetate. Calcium chloride is the preferred calcium component for the present invention. While phosphatidylserine is one preferred phospholipid for use in the invention, different phosphatidylserine species with different fatty acid groups, e.g., dioleoyl and dipalmitoyl, can also be employed. The inorganic phosphate may include, but is not limited to, ammonium acid phosphate, or an acid phosphate salt, as sodium (sodium phosphate) or potassium (potassium phosphate).

The complexed acidic phospholipid is prepared by mixing the salts and phospholipids, freezing the mixture, extracting the complex with organic solvents, and resuspending the final product for immediate use or storage. The mixing step achieves a uniform dispersion and allows the binding of the salts and phospholipids. To achieve binding of the calcium and phosphate to the phospholipids, the components are frozen under vacuum. In the freezing technique, the flask with the components is placed in a bath containing a slurry of acetone and dry ice or other appropriate freezing media. Any technique known in the art may be used to achieve the uniform dispersion, including but not limited to sonication, vortexing or homogenization methods. The dispersion contains an aqueous and organic phase. The organic, non-polar phase of the dispersion contains the desired complex. The aqueous or polar phase of the dispersion contains the unreacted salts, which is then immediately discarded. The complex of the organic, non-polar phase of the dispersion is extracted into an appropriate solvent from the reaction mixture. Appropriate solvents for use in the invention include, but are not limited to chloroform:methanol (2:1 v/v). Extraction methods useful in practicing the present invention include those well known in the art including but not limited to solvent extraction using phase separation techniques. The extracted complex can be dried under nitrogen, vacuum, evaporation or other methods known in the art. Purity may be assessed by using standard or routine techniques known and available to one skilled in the relevant art. These techniques include but are not limited to gas chromatography, thin layer chromatography, high performance liquid chromatography, and spectroscopy. In using two-dimensional thin-layer chromatography, the complex will not distribute in Getz solvents (G. S. Getz et al., Biochimica et Biophysica Acta, 1970) and therefore can be used to identify the presence of unincorporated phospholipids which would migrate in these solvents. After purity is assessed, the complex can be resuspended in a solution or solvent buffer, any of which may be commercially available.

In one specific embodiment, the complexed acidic phospholipid is prepared by adding up to 25 mg phosphatidylserine (commercially available from Avanti Polar Lipids, Alabama or another comparable source) to two buffered aqueous solutions (pH 7.4), the first to be added containing 1.5 mM ammonium acid phosphate, and the second containing 3 mM calcium chloride. The mixture is vortexed under vacuum in excess of 635 mm Hg to achieve cavitation, and then frozen rapidly in a dry ice acetone bath maintaining the vacuum. The mixture is then thawed, and the freeze-thaw sequence repeated, as necessary. The complexed acidic phospholipid is extracted from the aqueous solution in chloroform:methanol (2:1 v/v), and the extract is dried under nitrogen and then stored under vacuum to insure all solvents are removed. The complex is then resuspended in smaller volumes (e.g., 1-2 ml) of phosphate buffered saline (pH 7.4, 0.15M) or chloroform:methanol (2:1 v/v) for storage at a temperature of −20° C. In this manner, the complex may be stored indefinitely.

Collagen derived from any source is suitable for use within this invention, including insoluble collagen, acid-soluble collagen, collagen soluble in neutral or basic aqueous solutions, as well as those collagens which are commercially available (for example, from Becton Dickenson, Collagen Corp., Sigma-Aldrich, or Fujika). The collagen may come from mineralized or unmineralized collagen sources. Thus, the collagen may come from bone, tendons, skin, or the like, preferably type I collagen which involves a combination of two strands of α2 and one α1 collagen chains. The source of the collagen may be any convenient animal source, mammalian or avian, and may include bovine, porcine, equine, chicken, turkey, or other domestic source of collagen. Typical animal sources include but are not limited to calfskin, bovine Achilles tendon, cattle bones, and rat tail tendon. Type II or type IX collagen would come from cartilage of any of the above listed sources. Preferably the collagen is treated to eliminate any pathogens, e.g., viruses or prions.

In the preferred embodiment of the present invention, the collagen is type I collagen, although collagen types II and IX, or combinations thereof can also be employed in the invention. Type I collagen is used to repair or induce bone, dentin, or cementum growth; whereas types II and IX are used for the growth of calcifying cartilage. Collagen type I may be in the form of macroscopic fibers which can be chemically and mechanically separated from non-collagenous tissue components. In another embodiment, combinations of the collagen types may be used.

The collagen may be prepared by conventional purification methods available to one skilled in the art or can be purchased commercially as collagen sheets, sponges, or gels. In a preferred embodiment, collagen can be isolated from bone by a collagen extraction process involving EDTA decalcification, guanidine-hydrochloride extraction of non-collagenous proteins, and acetic acid solubilization of the remaining collagen (as described in Shigeyama et al., J. Periodontol. 1995, 66:478-87), or can be purchased commercially as collagen sheets or sponges. The insoluble collagenous tissue which is employed will normally be dispersed in a physiologically compatible buffer at an elevated pH. In one embodiment, the pH of the buffer is at least pH 8.

In one specific embodiment, rat tail collagen (commercially available from BD Biosciences) is dialyzed against water and redissolved in acetic acid (pH 3.5). The solution is then added to the complexed acidic phospholipid which has been dried under nitrogen. The acidic mixture is then vortexed and frozen rapidly under vacuum. After thawing, the pH is increased to 7.4. Alternatively, the composite formulation may be prepared in a basic environment by suspending dried complexed acidic phospholipid in PBS buffer (pH 7.4, 0.15M). The mixture is then vortexed and frozen rapidly under vacuum. After thawing, while maintaining a pH of approximately 8.0, collagen is then introduced into the solution. This formulation results in a gel-like preparation.

In specific embodiments, the complex may be adsorbed on to collagen fibers, collagen gels, or collagen sponges by adding the resuspended complex to the collagen, and rapidly freezing under vacuum. The complex binds avidly to collagen through non-covalent bonds to form the composite (See FIG. 1). The composite can be made with variable proportions of the complexed acidic phospholipid and collagen. Optimal binding depends on planned use, and the nature of the collagen substratum. In a preferred embodiment, in using collagen gels, 100 μg complexed acidic phospholipid can induce bone-like mineral formation when adsorbed on 10 mg of gelatin (Boskey, J Phys Chem, 1989, 93:1628-1633).

To facilitate clinical usage of the invention, the individual components of the composite, such as the collagen and the acidic phospholipid complex may be packaged separately in different forms and reconstituted and combined at the time of usage. Alternatively, the individual components may be added together and then packaged, as a premixed formulation. In particular, the premixed formulation provides the advantage of requiring minimal preparation by the individual clinician at the time of usage. For on-site preparation, the human collagen carrier/matrix and the complexed acidic phospholipid solution may be provided in freeze-dried aliquots and rehydrated just prior to being combined for use in clinical applications.

The prepared composite in the present invention is then deposited into the site of desired bone growth such as sites where tumors or bone cysts have been removed, or other bone or dentin defects. After placement of the composite, the affected area may be closed with a periosteal flap or other tissue specific method. The composite may be in the form of a paste, a sponge, a molded form, or preadsorbed onto another implant material. The form of the composite is determined by the size of the defect and other aspects of the application. The composite may also be encapsulated by a porous organic polymer for containment before placement at the desired site. Examples of such organic polymers include but are not limited to absorbable materials such as polyglycolic acid and nonabsorbable materials such as nylon or polypropylene. The compositions are useful in methods where they are applied to sites in humans or other mammals where bone formation and growth is desired. Examples of the use of the invention compositions given herein should be considered to be non-limiting. Due to the mineralization, the composite will persist until the tissue is remodeled by normal processes.

Practice of the invention requires the implantation of the composite, e.g., surgically, to serve as a template for bone formation in various orthopedic, periodontal, and reconstructive procedures or as a collagenous coating for implants. The invention compositions are useful, for example, at sites with bone defects due to surgery (as occurs, e.g., with the removal of a bone tumor), trauma, or a congenital deficiency (e.g., to correct a cleft palate). Periodontal applications include the use of the compositions to strengthen teeth implants and to surgically repair cut facial bones, e.g., mandibles during plastic surgery. The composite of the invention, has a gelatin-like consistency which can be altered by variation in water content, may be shaped as desired in anticipation of surgery or shaped by the physician or technician during surgery. The gelatin like composite can be precipitated by centrifugation, encapsulated in a porous organic polymer mold with the shape or geometry of the defect. The material may also be injected into a site where bone growth is desired. The composite can be kept in place by a periosteal flap, by sutures, or by a fibrin glue. Furthermore, the encapsulated composite form allows for the addition of other substances or materials, such as autologous osteoblasts or odontoblasts, antibiotics (e.g., tobramycin or penicillin (Callbiochem)), growth factor and cytokines (e.g., BMPs (Genetics Institute), FGFs or IGFs (Calbiochem)), and other nanomaterials such as carbon fibers or nanotubes (Zyvex, Nanolabs).

Alternatively, the composite may be coated or adsorbed on a prosthetic implant to promote implant/bone adhesion. Useful implants are constructed of inert materials such as ceramic, metals such as titanium, cadmium, nickel, or cobalt, or polymers such as polyglycolic acid or polylactic acid. The implant may be shaped to span a non-union fracture or to fill a bone defect. The material encourages cell motility, cellular biosynthetic functions, and cell division.

Hence, osteoblasts may be induced to migrate from viable bone to the material. Furthermore, osteoblasts synthesize fibronectin, a cellular adherence protein that binds collagen, thereby enhancing the ability of the migrating osteoblasts to adhere to the implant. In bone formation procedures, the composite material is slowly absorbed by the body and is replaced by bone in the shape of, or very nearly the shape of, the implant. The composite material also may be used for bone induction.

The composites of the present invention may be applied as a coating to an allograft or autograft used to fill in the defect, or at the junction of the graft and the native bone (the graft-host interface). Alternatively, the composites may be applied as a gel or as a rigid, bonelike structure, optionally surrounded and/or impregnated with more compositions to fill in undesired gaps. The rigid structure can serve as a bone replacement, providing strength and support until new bone replaces the structure. These rigid structures can, for example, serve as a bone strut, taking the shape of honeycombed tubular or flat structures. The rigid structures can also be formed into strong hollow tubes to be used as bridges. The rigid structures are also useful for forming an intervertebral fusion or a spinal prosthesis, e.g., after the removal of a disc, to maintain intervertebral spacing.

The composition may also be used at bone fractures to accelerate healing, or at the junctions between native bone and implants such as knee or hip replacements to prevent loosening of the prosthesis. In particular, use of the compositions of the present invention on fractures (e.g. of the vertebra, hip, or wrist) may be indicated for patients with osteoporosis, since the angiogenic and osteogenic properties of the compositions would be expected to strengthen osteoporotic bone advantageously. The present invention can also be used to enhance bone repair in mammals with bone fractures, defects or disorders resulting form weakened bones such as osteoarthritis, Paget's disease, osteomalacia, periodontal disease, bone loss from multiple myeloma and other forms of cancer, bone loss resulting from side effects of other medical procedures or treatment, and age-related loss of bone mass. The composite can also be used to repair osseous defects in the long, flat, and endochondral bones. Preventing the material from moving out of the defect site will depend upon the size and depth of the defect, and the nature of the site into which it is placed. In addition, the composite material of the present invention can be used to enhance bone growth into various prosthetic devices such that artificial parts and devices are permanently anchored into surrounding skeletal tissue through a natural osseous bridge.

The effective amounts of the composite used in the invention depend on the size of the defect and on the clinical application. In one preferred embodiment, the present invention can be used to correct defects in small structures such as teeth, hairline fractures, or small cysts. In this embodiment, the effective amounts would range between about 5 mg to about 5 g of the composition of the present invention.

In an alternative preferred embodiment, the present invention can be used to correct larger defects, such as large bones or implants. In this embodiment, the effective amounts would range between about 5 g and 100 g of the composition of the present invention.

Appropriate calculations are made based on the mathematical relationship between the density of the composite, mass and volume. Pre-clinical screening mechanisms, such as an MRI, may provide the necessary information relating to defect size and geometry which would enable one skilled in the art to determine the volume of the target defect and thus the necessary amount and shape of the composite.

The properties noted for acidic-phospholipid-complexes suggest that a complexed acidic phospholipid-collagen composite would be more osteoinductive than collagen itself, and/or than collagen with non-stable peptides. Because the complexed acidic phospholipid is not denatured using standard sterilization methods it provides a great advantage over the peptides being linked to collagen implants. These complexes can be made at relatively low cost, they are not readily degraded in vivo, and hence provide an excellent alternative to peptide-collagen composites.

The present invention provides a beneficial alternative to peptide-collagen composites at a low cost. The composition can be used in, but is not limited to, a method to repair bone and dentin defects as a result of surgical procedures or traumatic injuries, and a method to stimulate non-union fracture healing.

EXAMPLES

The present invention will be better understood by reference to the following Examples, which are provided as exemplary of the invention, and not by way of limitation.

Example 1

Formation of the Acidic Phospholipid Complex

This example demonstrates the formation of the acidic phospholipid complex used in the preparation of the composite with collagen.

The complexed acidic phospholipid is formed from a dried film of 25 mg dioleoyl phosphatidylserine in a buffered (pH 7.4) aqueous solution containing first 1.5 mM ammonium acid phosphate, to which 3 mM calcium chloride is then added. The phosphatidylserine is from Avanti Polar Lipids, Alabama or another comparable source. The components are placed under a vacuum in excess of 635 mm Hg, vortexed to achieve cavitation and then rapidly frozen in a dry ice acetone bath under vacuum. While maintaining the vacuum, the mixture is thawed and the freeze-thaw sequence repeated. After the second thaw, the complexed acidic phospholipid is extracted three times from the aqueous solution at room temperature using equal volumes of lipid solvent chloroform:methanol (2:1 v/v) and water. The extract is dried under nitrogen, and then under vacuum to insure all solvents are removed. The resulting product is weighed and its X-ray diffraction pattern determined. The X-ray diffraction pattern of the acidic phospholipid complex is shown in FIG. 2. The complex is then resuspended in 2-5 ml volumes of phosphate buffered saline or chloroform: methanol (2:1 v/v) for storage at a temperature of −20° C.

Example 2

Preparing of a Complexed Acidic Phospholipid-Collagen Composite

This example is designed to evaluate the ability of calcium-phospholipid-phosphate complex to readily bind to collagen.

5 mg of collagen dissolved in acetic acid pH 3.0 (commercially available from BD Biosciences) is dialyzed against 1.5 mM Tris buffer, rinsed and re-dissolved in 0.01 N acetic acid, pH 3.5. The limited acidity ensures that the complex does not break down during subsequent processing steps. The dissolved collagen is then added to 1500 μg dried complexed acidic phospholipid. The acidic mixture is vortexed and frozen rapidly under vacuum. After thawing, the pH is increased to 7.4.

Alternatively, a composite formulation is prepared in a basic environment by suspending 500 μg dried complexed acidic phospholipid in PBS buffer. While maintaining a pH of approximately 8.0, 5 mg of collagen is introduced into the solution. The mixture is frozen rapidly under vacuum. After thawing, the pH is adjusted to 7.4. This formulation results in a more viscous, gel-like preparation.

Composites can be made with variable proportions of the complexed acidic phospholipid and collagen, depending on planned use. The composite is then sterilized by gamma irradiation to provide a stable product that can be used for repair of bones. The composite is used to fill a defect site, and the process of healing demonstrated radiographically.

Optimal binding of complexed acidic phospholipid to collagen depends on planned use, and nature of the collagen substratum. If a collagen sponge is used, incubation with the sponge will take a longer time to insure incorporation of the complex than if the collagen is coprecipitated with the complex in solution. When a collagen gel or gel consisting of fibers is used, binding is more rapid, but the material will no longer be as easily molded unless preformed in a dissolvable porous mold.

Example 3

Cell Binding to Complexed Acidic Phospholipid Collagen Composite

This example demonstrates the binding ability of acidic phospholipid complex and rat collagen. This example is also designed to demonstrate that composites increase cell-binding and cell proliferation using human osteoblast-like cells, MG-63. Before usage, the prepared composite was sterilized under UV light. With MG-63 cell cultures, there is greater cell adherence and proliferation with the composite than either with a negative control or individual components of the composite or with a (positive) Fibronectin control.

When the composite was prepared in an acidic environment, the cells demonstrated adherence and proliferation (FIG. 3). When the composite was prepared in a basic environment, the cells also demonstrated adherence and proliferation (FIG. 4). However, when fibronectin was used, some cells remain in clumps and there appeared to be fewer cells that adhered compared to those exposed to either of the composite formulations (FIG. 5). Also, the negative control showed that the cells remain only in clumps and there appeared to be virtually no adherence or proliferation of the cells (FIG. 6).

Example 4

Accelerating Bone Formation

To demonstrate that the complexed acidic phospholipid-collagen composite accelerates bone formation by rat and human bone cells, the cultures described above are grown using the form of substratum which showed the maximum matrix formation. They are allowed to develop in the presence of 4 mM inorganic phosphate to favor mineral deposition. The mineralized matrices formed at days 11, 16, and 21 are compared using FTIR (Fourier transform infrared) microspectroscopy and imaging, to provide quantitative information on the amount of mineral formed, and the quality of the matrix. Electron microscopy is used to demonstrate that the mineral is aligned with the collagen, and thus is physiologic in nature. The complexed acidic phospholipid-collagen composite produces mineral more rapidly, and the mineralized matrix is more like bone (in terms of organization and composition) than the mineral (if any) formed on collagen alone.

Cell binding (based on DNA content) and cell maturation (based on alkaline phosphatase activity) by ROS 17.2.8 and SAOS cells (available from ATCC) are compared when the substratum is either type I collagen alone or the composite. The cell lines may be used to estimate the effective amounts to be used in patients. Using either rat (species specific) or synthetic complexed acidic phospholipid, composites consisting of complexed acidic phospholipid and type I collagen gel (Bloom Gelatin), complexed acidic phospholipid and macroporous collagen beads (BD), and collagen and fibril collagen (Collagen Corp.) are incubated with rat osteoblast-like cells for 9 days under standard conditions. Standard conditions for culturing osteoblasts include, but are not limited to, incubating monolayer cultures (30,000 cells/$cm^2$) at 37° C. and 5% carbon dioxide in media consisting of 10% fetal bovine serum (GIBCO), α-Modified Essential Medium (MEM) (GIBCO) supplemented with 3 nM Pi and 1 mM Ca, 25 μg/ml vitamin C (Calbiochem), 1 μM dexamethasone (Calbiochem), and 1.5% penicillin/streptomycin (GIBCO). DNA content, alkaline phosphatase activity, and cell morphology are evaluated.

Certain complexed acidic phospholipid-collagen composites show greater cell binding and more rapid maturation than collagen substrata alone. Macroporous collagen is the most effective.

Example 5

Use of Complexed Acidic Phospholipid Collagen Composite

This example describes how to use the composite in both a cartilage-cell and osteoblast-cell culture system, and after demonstration of efficacy, to implant this composite in bone and cartilage defects in animal models. The example demonstrates that the complexed acidic phospholipid-collagen composite accelerates bone formation in situ.

The success of the experiments in Examples 3 and 4 lead to the experimental treatment of an animal model. The rat bone defect fracture model developed by Lane et al., is used (Lane et al., Clin. Orthop. 1999, 361:216-227). The complexed acidic phospholipid-collagen composite is used to fill a 2 mm wide defect in the rat femur. Controls receive a comparable amount of collagen alone. The fracture defect site is plated, and rats examined radiographically over a 4 week period, at which point they will be sacrificed, and the mechanical properties of the healed femora compared. Additional assessment includes histology and FTIR microspectroscopy.

In many cases the complexed acidic phospholipid-collagen composite results in more rapid healing, and that at the selected time point, the bones with the composite resist load better than those with repaired with the collagen alone.

Other experiments include the use of the composite in a calvarial defect model (intramembranous ossification) (Schmitz et al., Acta Anat (Basel) 1990;138:185-92), in a growth plate lesion or fracture model (endochondral ossification) (Bostrom et al., J Orthop Res. 1995; 13:357-67), and in a dentin injury model (dentin repair/odontogenesis)

(Hunter et al., Endod Dent Traumatol. 1998;14:112-8; Sloan et al., Arch Oral Biol. 2000; 45:173-7.; Costa et al., Am J Dent. 2000;13:81-7).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A composition for osteoinduction which comprises a composite material comprising an acidic-phospholipid complex and fibrillar collagen, wherein the complex comprises calcium, phospholipids, and inorganic phosphate, and wherein the fibrillar collagen is type I collagen, type II collagen, type IX collagen, or a mixture thereof.

2. The composition of claim 1, wherein the complex comprises calcium, phospholipid, and inorganic phosphate in a molar ratio range of 45-55 parts calcium:35-45 parts phospholipid:5-15 parts inorganic phosphate, respectively.

3. The composition of claim 1, wherein the complex comprises calcium, phospholipid, and inorganic phosphate in a molar ratio range of 47-53 parts calcium:38-42 parts phospholipid:8-12 parts inorganic phosphate, respectively.

4. The composition of claim 1, wherein the complex comprises calcium, phospholipid, and inorganic phosphate in a molar ratio of 50 parts calcium:40 parts phospholipid: 10 parts inorganic phosphate, respectively.

5. The composition of claim 1, wherein the calcium is calcium chloride or soluble calcium salts of any other weak or strong acid.

6. The composition of claim 5, wherein the calcium salt is calcium nitrate.

7. The composition of claim 5, wherein the calcium salt is calcium acetate.

8. The composition of claim 1, wherein the phospholipid is phosphatidylserine.

9. The composition of claim 8, wherein the phosphatidylserine has fatty acid chains, which have at least 12 carbons per chain that are identical or different, saturated or unsaturated.

10. The composition of claim 1, wherein the inorganic phosphate is ammonium acid phosphate.

11. The composition of claim 1, wherein the inorganic phosphate is an acid phosphate salt.

12. The composition of claim 11, wherein the acid phosphate salt is sodium phosphate.

13. The composition of claim 11, wherein the acid phosphate salt is potassium phosphate.

14. The composition of claim 1, wherein the collagen is type I collagen.

15. The composition of claim 1, wherein the collagen is type II collagen.

16. The composition of claim 1, wherein the collagen is type IX collagen.

17. The composition of claim 1, wherein the collagen is a mixture of type II and type IX collagen.

18. A method for inducing the growth of mineralized tissue in a mammal comprising applying an effective growth stimulating amount of a complexed-acidic-phospholipid-collagen composite at a site in need of desired mineralized tissue growth selected from the group consisting of bone, calcifying cartilage, dentin and cementum wherein the complexed-acidic-phospholipid-collagen composite comprises calcium, phospholipid, inorganic phosphate, and fibrillar collagen, wherein the fibrillar collage is type I collagen, type II coallgen, type IX collagen, or a mixture thereof.

19. The method of claim 18, wherein the composite is in paste form, sponge form, molded form, or preadsorbed onto an implant material.

20. The method of claim 18, wherein the composite is encapsulated by an organic polymer.

21. The method of claim 20, wherein the organic polymer is selected from polyglycolic acid, nylon, and polypropylene.

22. The method of claim 20, further comprising one or more materials selected from the group consisting of autologous osteoblasts, odontoblasts, antibiotics, growth factors, cytokines, carbon fibers, and nanotubes.

23. The method of claim 18, wherein said effective growth stimulating amount ranges between about 5 mg and about 5g.

24. The method of claim 18, wherein said effective growth stimulating amount ranges between about 5 g and about 100g.

* * * * *